United States Patent [19]
Rollmann
[11] 4,088,605
[45] May 9, 1978

[54] ZSM-5 CONTAINING ALUMINUM-FREE SHELLS ON ITS SURFACE

[75] Inventor: Louis D. Rollmann, Princeton, N.J.
[73] Assignee: Mobil Oil Corporation, New York, N.Y.

[21] Appl. No.: 726,353
[22] Filed: Sep. 24, 1976
[51] Int. Cl.[2] ........................ B01J 29/06; C01B 33/28
[52] U.S. Cl. ................................. 252/455 Z; 423/328
[58] Field of Search ..................... 252/455 Z; 423/328

[56] References Cited

U.S. PATENT DOCUMENTS 3,275,571 9/1966 Mattox ............................ 252/455 Z

*Primary Examiner*—Carl F. Dees
*Attorney, Agent, or Firm*—Charles A. Huggett; Raymond W. Barclay; Claude E. Setliff

[57] ABSTRACT

Aluminosilicate zeolites are prepared containing an outer aluminum-free shell. The outer shell is essentially $SiO_2$ that has crystallized on the zeolite surface in the ZSM-5 type configuration, leading to a more selective catalyst.

20 Claims, No Drawings

ZSM-5 CONTAINING ALUMINUM-FREE SHELLS ON ITS SURFACE

BACKGROUND OF THE INVENTION

1. Field of the Invention

This invention relates to crystalline aluminosilicate zeolites and to the synthesis thereof. It more particularly relates to the synthesis of a zeolite containing an outer shell free from aluminum. The invention further relates to the product of such synthesis.

2. Discussion of the Prior Art

Certain of the zeolites disclosed herein and their synthesis are well known. Examples are ZSM-5 and ZSM-11. These zeolites are fully described in U.S. Pat. Nos. 3,702,886 and 3,709,979. They are known to have catalytic capabilities for various conversion reactions. Because of their ordered, porous structure, creating small interconnected cavities, they are selective toward certain molecules. That is to say, the pores accept for adsorption molecules of certain dimensions while rejecting those of larger dimensions. However, no known art discloses or suggests increasing selectivity by essentially inactivating the surface of the catalyst with an isocrystalline layer of aluminum-free zeolite.

SUMMARY OF THE INVENTION

In accordance with the invention there is provided a crystalline aluminosilicate zeolite having an aluminum-free outer shell of crystalline $SiO_2$, the zeolite being made by a two-stage method comprising:

(1) initiating crystallization in a crystallization medium to produce the zeolite and then (2) altering the crystallization medium to eliminate the aluminum therein, wherein said outer shell of $SiO_2$ has the same crystal structure as said zeolite. In many cases it will also be desirable to increase the hydroxide content and/or to reduce the organic ion, i.e., the template ion, to $SiO_2$ ratio.

DESCRIPTION OF SPECIFIC EMBODIMENTS

The zeolite catalysts useful herein are ZSM-5 type zeolites and are members of a class of zeolites exhibiting some unusual properties. They are useful in cracking and hydrocracking and are outstandingly useful in other petroleum refining processes, indicating again the unique catalytic characteristics of this family of zeolites. The later processes include isomerization of n-paraffins and naphthenes, polymerization of compounds containing an olefinic or acetylenic carbon to carbon linkage such as isobutylene and butene-1, reforming, alkylation, isomerization of polyalkyl substituted aromatics, e.g., ortho xylene, aromatics alkylation, such as reaction of benzene with ethylene, disproportionation of aromatics such as toluene to provide a mixture of benzene, xylenes and higher methylbenzenes, as well as conversion of polar compounds such as methanol to hydrocarbon products. They have exceptional high selectivity and under the conditions of hydrocarbon conversion provide a high percentage of desired products relative to total products compared with known zeolitic hydrocarbon conversion.

Although they have unusually low alumina contents, i.e. high silica to alumina ratios, they are very active even when the silica to alumina ratio exceeds 30. The activity is surprising since catalytic activity is generally attributed to framework aluminum atoms and cations associated with these aluminum atoms. These catalysts retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from, the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type catalysts useful in this invention possess, in combination: a silica to alumina ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although catalysts with a silica to alumina ratio of at least 12 are useful, it is preferred to use catalysts having higher ratios of at least about 30. Such catalysts, after activation, acquire an intracrystalline sorption capacity for normal hexane which is greater than that for water, i.e. they exhibit "hydrophobic" properties. It is believed that this hydrophobic character is advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although, in some instances, excessive puckering or pore blockage may render these catalysts ineffective. Twelve-membered rings do not generally appear to offer sufficient constraint to produce the advantageous conversions, although puckered structures exist such as TMA offretite which is a known effective zeolite. Also, structures can be conceived, due to pore blockage or other cause, that may be operative.

Rather than attempt to judge from crystal structure whether or not a catalyst possesses the necessary constrained access, a simple determination of the "constraint index" may be made by passing continuously a mixture of an equal weight of normal hexane and 3-methylpentane over a small sample, approximately 1 gram or less, of catalyst at atmospheric pressure according to the following procedure. A sample of the catalyst, in the form of pellets or extrudate, is crushed to a particle size about that of coarse sand and mounted in a glass tube. Prior to testing, the catalyst is treated with a stream of air at 1000° F for at least 15 minutes. The catalyst is then flushed with helium and the temperature adjusted between 550° and 950° F to give an overall conversion between 10% and 60%. The mixture of hydrocarbons is passed at 1 liquid hourly space velocity (i.e., 1 volume of liquid hydrocarbon per volume of catalyst per hour) over the catalyst with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10} (\textit{fraction of n-hexane remaining})}{\log_{10} (\textit{fraction of 3-methylpentane remaining})}$$

The constraint index approximates the ratio of the cracking rate constants for the two hydrocarbons. Catalysts suitable for the present invention are those having a constraint index in the approximate range of 1 to 12. Constraint Index (CI) values for some typical catalysts are:

| CAS | C.I. |
|---|---|
| ZSM-5 | 8.3 |
| ZSM-11 | 8.7 |
| ZSM-12 | 2 |
| ZSM-21 | 4.5 |
| ZSM-35 | 4.5 |
| TMA Offretite | 3.7 |
| Beta | 0.6 |
| ZSM-4 | 0.5 |
| H-Zeolon | 0.5 |
| REY | 0.4 |
| Amorphous Silica-Alumina | 0.6 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550° to 950° F, with accompanying conversion between 10% and 60%, the constraint index may vary within the indicated approximate range of 1 to 12. Likewise, other variables such as the crystal size of the zeolite, the presence of possibly occluded contaminants and binders intimately combined with the zeolite may affect the constraint index. it will accordingly be understood by those skilled in the art that the constraint index, as utilized herein, while affording a highly useful means for characterizing the zeolites of interest is approximate, taking into consideration the manner of its determination, with the probability, in some instances, of compounding variable extremes. However, in all instances, at a temperature within the above-specified range of 550° to 950° F, the constraint index will have a value for any given zeolite of interest herein within the approximate range of 1 to 12.

The class of zeolites defined herein is defined by ZSM-5, ZSM-11, ZSM-12, ZSM-21 and ZSM-35. U.S. Pat. No. 3,702,886, as mentioned above, describes and claims ZSM-5. The patent is incorporated herein by reference.

ZSM-5 type zeolite compositions have the characteristic X-ray diffraction pattern set forth in Table 1, hereinbelow. ZSM-5 itself can also be identified, in terms of mole ratios of oxides as follows:

$$0.9 \pm 0.2M_{2/n}O:W_2O_3:3\text{-}1000YO_2:zH_2O$$

wherein M is a cation, *n* is the valence of said cation, W is aluminum, Y is silicon, and *z* is from 0 to 40. In a preferred synthesized form, the zeolite has a formula, in terms of mole ratios of oxides, as follows:

$$0.9 \pm 0.2M_{2/n}O:Al_2O_3:5\text{-}500SiO_2:zH_2O$$

and M is selected from the group consisting of a mixture of alkali metal cations, especially sodium, and organic ions, such as tetraalkylammonium cations, the alkyl groups of which preferably contain 2–5 carbon atoms.

The original cations can be replaced in accordance with technques well-known in the art, at least in part, by ion exchange with other cations. Preferred replacing cations include tetraalkylammonium cations, metal ions, ammonium ions, hydrogen ions, and mixtures of the same. Particularly preferred cations are those which render the zeolite catalytically active, especially for hydrocarbon conversion. These include hydrogen, rare earth metals, aluminum, metals of Groups II and VIII of the Periodic Table.

In a preferred embodiment of ZSM-5, W is aluminum, Y is silicon and the silica/alumina mole ratio is at least 10 and ranges up to about 300.

ZSM-5 type zeolites have an exceptionally high degree of thermal stability, thereby rendering them particularly effective for use in processes involving elevated temperatures. In this connection, ZSM-5 type zeolites appear to be one of the most stable families of zeolites known to date.

ZSM-5 zeolite possesses a definite distinguishing crystalline structure whose X-ray diffraction pattern shows the following significant lines:

TABLE 1

| Interplanar Spacing d(A) | Relative Intensity |
|---|---|
| 11.1 ± 0.2 | s. |
| 10.0 ± 0.2 | s. |
| 7.4 ± 0.15 | w. |
| 7.1 ± 0.15 | w. |
| 6.3 ± 0.1 | w. |
| 6.04 / 5.97 } ± 0.1 | w. |
| 5.56 ± 0.1 | w. |
| 5.01 ± 0.1 | w. |
| 4.60 ± 0.08 | w. |
| 4.25 ± 0.08 | w. |
| 3.85 ± 0.07 | v.s. |
| 3.71 ± 0.05 | s. |
| 3.04 ± 0.03 | w. |
| 2.99 ± 0.02 | w. |
| 2.94 ± 0.02 | w. |

These values were determined by standard techniques. The radiation was the K-alpha doublet of copper, and a scintillation counter spectrometer with a strip chart pen recorder was used. The peak heights, I, and the positions as a function of 2 times theta, where theta is the Bragg angle were read from the spectrometer chart. From these, the relative intensities, 100 $I/I_o$ where $I_o$ is the intensity of the strongest line or peak, and *d* (obs.), the interplanar spacing in A, corresponding to the recorded lines, were calculated. In Table 1 the relative intensities are given in terms of the symbols s. = strong, m. = medium, m.s. = medium strong, m.w. = medium weak and v.s. = very strong. It should be understood that this X-ray diffraction pattern is characteristic of all the species of ZSM-5 compositions. Ion exchange of the sodium ion with cations reveals substantially the same pattern with some minor shifts in interplanar spacing and variation in relative intensity. Other minor variations can occur depending on the silicon to aluminum ratio of the particular sample and on whether it had been subjected to thermal treatment.

Various cation exchanged forms of ZSM-5 have been prepared. X-ray powder diffraction patterns of several of these forms of ZSM-5 are set forth fully in U.S. Pat. No. 3,702,886.

Zeolite ZSM-5 per se can be suitably prepared by preparing a solution containing tetrapropyl ammonium hydroxide, sodium oxide, an oxide of aluminum, an oxide of silica, and water and having a composition, in terms of mole ratios of oxides, falling within the following ranges:

TABLE 2

| | Broad | Preferred | Particularly Preferred |
|---|---|---|---|
| $\frac{OH^-}{YO_2}$ | 0.02–10.0 | 0.05–0.8 | 0.2–0.75 |
| $\frac{R_4N^+}{(R_4N^+ + Na^+)}$ | 0.01–0.95 | 0.02–0.6 | 0.05–0.4 |
| $\frac{H_2O}{OH^-}$ | 10–1000 | 30–700 | 50–500 |
| $\frac{YO_2}{W_2O_3}$ | 5–2000 | 10–500 | 20–150 |

wherein R is propyl, W is aluminum and Y is silicon maintaining the mixture until crystals of the zeolite are formed. It is noted that an excess of tetrapropylammonium hydroxide can be used which would raise the value of OH—/$YO_2$ above the ranges set forth supra. The excess hydroxide, of course, does not participate in the reaction. Thereafter, the crystals are separated from the liquid and recovered. Typical reaction conditions consist of heating the foregoing reaction mixture to a temperature of from about 80° C to 200° C for a period of time of from about four hours to 180 days. A more preferred temperature range is from about 150° to 175° C with the amount of time at a temperature in such range being from about 4 hours to 8 days.

The digestion of the gel particles is carried out until crystals form. The solid product is separated from the reaction medium, as by cooling the whole to room temperature, filtering, and water washing.

The foregoing product is dried, e.g., at 230° F, for from about 2 to 24 hours. Of course, milder conditions may be employed if desired, e.g., room temperature under vacuum.

The zeolites are obviously formed as aluminosilicates. The specific composition can be prepared utilizing materials which supply the appropriate oxide. Such compositions include, for an aluminosilicate, sodium aluminate, alumina, sodium silicate, silica hydrosol, silica gel, silicic acid, sodium hydroxide and tetrapropylammonium hydroxide. It will be understood that each oxide component utilized in the reaction mixture for preparing the zeolite can be supplied by one or more initial reactants and they can be mixed together in any order. For example, sodium oxide can be supplied by an aqueous solution of sodium hydroxide, or by an aqueous solution of sodium silicatetetrapropylammonium cation can be supplied by the bromide salt. The reaction mixture can be prepared either batchwise or continuously. Crystal size and crystallization time of the ZSM-5 composition will vary with the nature of the reaction mixture employed.

ZSM-11 is described in U.S. Pat. No. 3,709,979, the entire contents of which are incorporated herein by reference.

ZSM-12 is described in U.S. Pat. No. 3,832,449, the entire contents of which are incorporated herein by reference.

ZSM-21 is described in U.S. application Ser. No. 528,060 (Mobil Docket 8713), filed November 29, 1974. This zeolite can be identified, in terms of mole ratios of oxides and in the anhydrous state, as follows:

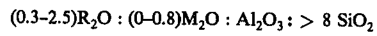

$$(0.3\text{–}2.5)R_2O : (0\text{–}0.8)M_2O : Al_2O_3 : > 8\ SiO_2$$

wherein R is an organic nitrogen-containing cation derived from a 2-(hydroxyalkyl) trialkylammonium compound and M is an alkali metal cation, and is characterized by a specified X-ray powder diffraction pattern.

In a preferred synthesized form, the zeolite has a formula, in terms of mole ratios of oxides and in the anhydrous state, as follows:

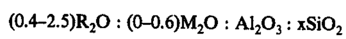

$$(0.4\text{–}2.5)R_2O : (0\text{–}0.6)M_2O : Al_2O_3 : xSiO_2$$

wherein R is an organic nitrogen-containing cation derived from a 2-(hydroxyalkyl)trialkylammonium compound, wherein alkyl is methyl, ethyl or a combination thereof, M is an alkali metal, especially sodium, and $x$ is from greater than 8 to about 50.

The synthetic ZSM-21 zeolite possesses a definite distinguishing crystalline structure whose X-ray diffraction pattern shows substantially the significant lines set forth in Table 3. It is observed that this X-ray diffraction pattern (significant lines) is similar to that of natural ferrierite with a notable exception being that natural ferrierite patterns exhibit a significant line at 11.33A.

TABLE 3

| Interplanar Spacing d(A) | Relative Intensity |
|---|---|
| 9.8 ± 0.20 | s. |
| 9.1 ± 0.19 | m. |
| 8.0 ± 0.16 | w. |
| 7.1 ± 0.14 | m. |
| 6.7 ± 0.14 | m. |
| 6.0 ± 0.12 | w. |
| 4.37 ± 0.09 | w. |
| 4.23 ± 0.09 | w. |
| 4.01 ± 0.08 | v.s. |
| 3.81 ± 0.08 | v.s. |
| 3.69 ± 0.07 | m. |
| 3.57 ± 0.07 | v.s. |
| 3.51 ± 0.07 | v.s. |
| 3.34 ± 0.07 | m. |
| 3.17 ± 0.06 | s. |
| 3.08 ± 0.06 | m. |
| 3.00 ± 0.06 | w. |
| 2.92 ± 0.06 | m. |
| 2.73 ± 0.06 | w. |
| 2.66 ± 0.05 | w. |
| 2.60 ± 0.05 | w. |
| 2.49 ± 0.05 | w. |

A further characteristic of ZSM-21 is its sorptive capacity providing said zeolite to have increased capacity for 2-methylpentane (with respect to n-hexane sorption by the ratio n-hexane/2-methyl-pentane) when compared with a hydrogen form of natural ferrierite resulting from calcination of an ammonium exchanged form. The characteristic sorption ratio n-hexane/2-methylpentane for ZSM-21 (after calcination at 600° C) is less than 10, whereas that ratio for the natural ferrierite is substantially greater than 10, for example, as high as 34 or higher.

Zeolite ZSM-21 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| R+ | Broad | Preferred |
|---|---|---|
| $\frac{R+}{R+ + M+}$ | 0.2-1.0 | 0.3-0.9 |
| $\frac{OH^-}{SiO_2}$ | 0.05-0.5 | 0.07-0.49 |
| $\frac{H_2O}{OH^-}$ | 41-500 | 100-250 |
| $\frac{SiO_2}{Al_2O_3}$ | 8.8-200 | 12-60 |

wherein R is an organic nitrogen-containing cation derived from a 2-(hydroxyalkyl) trialkylammonium compound and M is an alkali metal ion, and maintaining the mixture until crystals of the zeolite are formed. (The quantity of $OH^-$ is calculated only from the inorganic sources of alkali without any organic base contribution). Thereafter, the crystals are separated from the liquid and recovered. Typical reaction conditions consist of heating the foregoing reaction mixture to a temperature of from about 90° to about 400° C for a period of time of from about 6 hours to about 100 days. A more preferred temperature range is from about 150° to about 400° C with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is thereafter dried, e.g., at 230° F for from about 8 to 24 hours.

ZSM-35 is more particularly described in U.S. application Ser. No. 528,061 (Mobil Docket 8714), filed Nov. 29, 1974. This zeolite can be identified, in terms of mole ratio of oxides and in the anhydrous state, as follows:

$$(0.3\text{-}2.5)R_2O : (0\text{-}0.8)M_2O : Al_2O_3 : >8\ SiO_2$$

wherein R is an organic nitrogen-containing cation derived from etheylenediamine or pyrrolidine and M is an alkali metal cation, and is characterized by a specified X-ray powder diffraction pattern.

In a preferred synthesized form, the zeolite has a formula, in terms of mole ratios of oxides and in the anhydrous state, as follows:

$$(0.4\text{-}2.5)R_2O : (0\text{-}0.6)M_2O : Al_2O_3 : xSiO_2$$

wherein R is an organic nitrogen-containing cation derived from ethylenediamine or pyrrolidine, M is an alkali metal, especially sodium, and $x$ is from greater than 8 to about 50.

The synthetic ZSM-35 zeolite possesses a definite distinguishing crystalline structure whose X-ray diffraction pattern shows substantially the significant lines set forth in Table 4. It is observed that this X-ray diffraction pattern (with respect to significant lines) is similar to that of natural ferrierite with a notable exception being that natural ferrierite patterns exhibit a significant line at 11.33A. Close examination of some individual samples of ZSM-35 may show a very weak line at 11.3-11.5A. This very weak line, however, is determined not to be a significant line for ZSM-35.

TABLE 4

| Interplanar Spacing d(A) | Relative Intensity |
|---|---|
| 9.6 ± 0.20 | v.s. - v.v.s. |
| 7.10 ± 0.15 | m. |
| 6.98 ± 0.14 | m. |
| 6.64 ± 0.14 | m. |
| 5.78 ± 0.12 | w. |
| 5.68 ± 0.12 | w. |
| 4.97 ± 0.10 | w. |
| 4.58 ± 0.09 | w. |
| 3.99 ± 0.08 | s. |
| 3.94 ± 0.08 | m.s. |
| 3.85 ± 0.08 | m. |
| 3.78 ± 0.08 | s. |
| 3.74 ± 0.08 | w. |
| 3.66 ± 0.07 | m. |
| 3.54 ± 0.07 | v.s. |
| 3.48 ± 0.07 | v.s. |
| 3.39 ± 0.07 | w. |
| 3.32 ± 0.07 | w.m. |
| 3.14 ± 0.06 | w.m. |
| 2.90 ± 0.06 | w. |
| 2.85 ± 0.06 | w. |
| 2.71 ± 0.05 | w. |
| 2.65 ± 0.05 | w. |
| 2.62 ± 0.05 | w. |
| 2.58 ± 0.05 | w. |
| 2.54 ± 0.05 | w. |
| 2.48 ± 0.05 | w. |

A further characteristic of ZSM-35 is its sorptive capacity proving said zeolite to have increased capacity for 2-methylpentane (with respect to n-hexane sorption by the ratio n-hexane/2-methylpentane) when compared with a hydrogen form of natural ferrierite resulting from calcination of an ammonium exchanged form. The characteristic sorption ratio n-hexane/2-methylpentane for ZSM-35 (after calcination at 600° C) is less than 10, whereas that ratio for the natural ferrierite is substantially greater than 10, for example, as high as 34 or higher.

Zeolite ZSM-35 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| R+ | Broad | Preferred |
|---|---|---|
| $\frac{R+}{R+ + M+}$ | 0.2-1.0 | 0.3-0.9 |
| $\frac{OH^-}{SiO_2}$ | 0.05-0.5 | 0.07-0.49 |
| $\frac{H_2O}{OH^-}$ | 41-500 | 100-250 |
| $\frac{SiO_2}{Al_2O_3}$ | 8.8-200 | 12-60 |

wherein R is an organic nitrogen-containing cation derived from pyrrolidine or ethylenediamine and M is an alkali metal ion, and maintaining the mixture until crystals of the zeolite are formed. (The quantity of $OH^-$ is calculated only from the inorganic sources of alkali without any organic base contribution). Thereafter, the crystals are separated from the liquid and recovered. Typical reaction conditions consist of heating the foregoing reaction mixture to a temperature of from about 90° to about 400° C for a period of time of from about 6 hours to about 100 days. A more preferred temperature range is from about 150° to about 400° C with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is dried, e.g. at 230° F, for from about 8 to 24 hours.

The specific zeolites described, when prepared in the presence of organic cations, are catalytically inactive, possibly because the intracrystalline free space is occupied by organic cations from the forming solution. They may, however, be activated by heating in an inert atmosphere at 1000° F for one hour, followed by base exchange with ammonium salts and followed by a further calcination at 1000° F in air.

The zeolites can be used either in the alkali metal form, e.g., the sodium form, the ammonium form, the hydrogen form, or another univalent or multivalent cationic form. Preferably, one or the other of the last two forms is employed. They can also be used in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such component can be exchanged into the composition, impregnated therein or physically intimately admixed therewith. Such component can be impregnated in or on to the present catalyst such as, for example, by in the case of platinum, treating the zeolite with a platinum metal-containing ion. Thus, suitable platinum compounds include chloroplatinic acid, platinous chloride and various compounds containing the platinum amine complex.

The compounds of the useful platinum or other metals can be divided into compounds in which the metal is present in the cation of the compound and compounds in which it is present in the anion of the compound. Both types which contain the metal in the ionic state can be used. A solution in which platinum metals are in the form of a cation or cationic complex, e.g., $Pt(NH_3)_6Cl_4$ is particularly useful. For some hydrocarbon conversion processes, this noble metal form of the catalyst is unnecessary such as in low temperature, liquid phase ortho xylene isomerization.

The catalyst, when employed either as an absorbent or as a catalyst in one of the aforementioned processes, should be dehydrated at least partially. This can be done by heating to a temperature in the range of 200° to 600° C in an atmosphere such as air, nitrogen, etc., and at atmospheric or subatmospheric pressures for between 1 and 48 hours. Dehydration can also be performed at lower temperatures merely by placing the catalyst in a vacuum, but a longer time is required to obtain a sufficient amount of dehydration.

In a preferred aspect of this invention, the catalysts hereof are selected as those having a crystal framework density, in the dry hydrogen form, of not substantially below about 1.6 grams per cubic centimeter. It has been found that zeolites which satisfy all three of these criteria are most desired because they tend to maximize the production of gasoline boiling range hydrocarbon products. Therefore, the preferred catalysts of this invention are those having a constraint index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on page 19 of the article on Zeolite Structure by W. M. Meir. This paper, the entire contents of which are incorporated herein by reference, is included in "Proceedings of the Conference on Molecular Sieves, London, April 1967", published by the Society of Chemical Industry, London, 1968. When the crystal structure is unknown, the crystal framework density may be determined by classical pykometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density of course must be associated with a relatively small amount of free space within the crystal, which might be expected to result in more stable structures. This free space, however, is important as the locus of catalytic activity.

Following the completion of synthesizing the zeolite, it is essential, for the purposes of this invention, to reduce or eliminate the nucleation of the aluminosilicate while at the same time keeping the crystal growth high. To produce the outer aluminum-free shell, it is also essential that the reactive aluminum be removed from the reaction mixture.

It is therefore necessary to process the zeolite and to replace the crystallization medium with an aluminum-free mixture to obtain crystallization of $SiO_2$ on the surface of the zeolite, the $SiO_2$ having the same crystal structure as the zeolite. This can be accomplished by a total replacement of the reaction mixture or by complexing from the original reaction mixture any remaining aluminum ion with reagents such as gluconic acid, tartaric acid, nitrilotriacetic acid or EDTA. In addition, the $OH^-$ concentration must be increased and the organic ion reduced so that the new reaction mixture, exclusive of solid crystals, has the following composition, in terms of mole ratios of oxides:

TABLE 5

| | Broad | Preferred | Particularly Preferred |
|---|---|---|---|
| $\frac{R^*}{SiO_2}$ | 0.01–0.10 | 0.01–.08 | 0.02–0.06 |
| $\frac{SiO_2}{Al_2O_3}$ | 300–5000 | 500–5000 | 700–5000 |
| $\frac{H_2O}{OH^-}$ | 20–500 | 50–300 | 60–250 |
| $\frac{OH^-}{SiO_2}$ | 0.05–1 | 0.1–0.8 | 0.2–0.6 |
| $\frac{M_2O}{SiO_2}$ | .1–2 | 0.15–1.5 | 0.2–1 |

* R is an organic ion.

These ranges apply to the contemplated zeolite ZSM-5, ZSM-11, ZSM-12, ZSM-21 and ZSM-35. Typical reaction conditions include heating the above mixture at a temperature of from about 80° to about 200° C for a period of time from about 4 hours to about 30 days. As in the case of ZSM-5 aluminosilicate synthesis, the digestion of the gel particles is carried out until the crystalline $SiO_2$ forms completely on the outer shell of the zeolite particles. The product crystals are then separated, as by cooling and filtering, and are water washed and dried at from about 80° to about 150° C.

Members of the present family of zelites can have the original cations associated therewith replaced by a wide variety of other cations according to techniques well known in the art. Typical replacing cations would include hydrogen, ammonium and metal cations including mixtures of the same. Of the replacing metallic cations, particular preference is given to cations of metals such as rare earth metals, manganese and calcium, as well as metals of Group II of the Periodic Table, e.g., zinc and Group VIII of the Periodic Table, e.g., nickel.

Typical ion exchange techniques include contacting the members of the family of zeolites with a salt of the desired replacing cation or cations. Although a wide variety of salts can be employed, particular preference is given to chlorides, nitrates and sulfates.

Representative ion exchange techniques are disclosed in a wide variety of patents including U.S. Pat. Nos. 3,140,249; 3,140,251; and 3,140,253.

Following contact with the salt solution of the desired replacing cation, the zeolites are then preferably washed with water and dried at a temperature ranging from 150° to about 600° F and thereafter calcined in air or other inert gas at temperatures ranging from about 500° to about 1500° F for periods of time ranging from 1 to 48 hours or more.

Regardless of the cations replacing the sodium in the synthesized form of the catalyst, the spatial arrangement of the aluminum, silicon and oxygen atoms which form the basic crystal lattices in any given zeolite of this invention remains essentially unchanged by the described replacement of sodium or other alkali metal as determined by taking an X-ray powder diffraction pattern of the ion-exchanged material. For example, the X-ray diffraction pattern of several ion-exchanged ZSM-5 zeolites reveal a pattern substantially the same as that set forth in Table 1, above.

The aluminosilicates prepared by the instant invention are formed in a wide variety of particular sizes. Generally speaking, the particles can be in the form of a powder, a granule, or a molded product, such as extrudate having particle size sufficient to pass through a 2 mesh (Tyler) screen and be retained on a 400 mesh (Tyler) screen. In cases where the catalyst is molded, such as by extrusion, the aluminosilicate can be extruded before drying or dried or partially dried and then extruded.

In the case of many catalysts, it is desired to incorporate the catalyst of this invention with another material resistant to the temperatures and other conditions employed in organic conversion processes. Such materials include active and inactive materials and synthetic or naturally occurring zeolites as well as inorganic materials such as clays, silica and/or metal oxides. The latter may be either naturally occurring or in the form of gelatinous precipitates or gels including mixtures of silica and metal oxides. Use of a material in conjunction with the present catalyst tends to improve the conversion and/or selectivity of the catalyst in certain organic conversion processes. Inactive materials suitably serve as diluents to control the amount of conversion in a given process so that products can be obtained economically and in orderly manner without employing other means for controlling the rate of reaction. Normally, zeolite materials have been incorporated into naturally occurring clays, e.g., bentonite and kaolin, to improve the crush strength of the catalyst under commercial operating conditions. These materials, i.e., clays, oxides, etc. function as binders for the catalyst. It is desirable to provide a catalyst having good crush strength, because in a petroleum refinery the catalyst is often subjected to rough handling, which tends to break the catalyst down into powder-like materials which cause problems in processing. These clay binders have been employed for the purpose of improving the crush strength of the catalyst.

Naturally occurring clays which can be composited with the catalyst include the montmorillonite and kaoline family, which families include the sub-bentonites, and the kaolins commonly known as Dixie McNamee-Georgia and Florida clays or others in which the main mineral constituent is halloysite, kaolinite, dickite, nacrite, or anauxite. Such clays can be used in the raw state as originally mined or initially subjected to calcination, acid treatment or chemical modification.

In addition to the foregoing materials, the catalyst can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The matrix can be in the form of a cogel. The relative proportions of the finely divided crystalline aluminosilicate containing the aluminum-free outer shell and inorganic oxide gel matrix vary widely with the crystalline aluminosilicate content ranging from about 1 to about 90 percent by weight and more usually, particularly when the composite is prepared in the form of beads in the range of about 2 to about 50 percent by weight of the composite.

Employing the catalyst of this invention containing a hydrogenation component, heavy petroleum residual stocks, cycle stocks, and other hydrocrackable charge stocks can be hydrocracked at temperatures between 400° and 850° F using molar ratios of hydrogen to hydrocarbon charge in the range between 2 and 80. The pressure employed will vary between 10 and 2,500 psig and the liquid hourly space velocity between 0.1 and 10.

Employing the catalyst of this invention for catalytic cracking, hydrocarbon cracking stocks can be cracked at a liquid hourly space velocity between about 0.5 and 50, a temperature between about 550° and 1300° F, a pressure between about atmospheric and a hundred atmospheres.

Employing a catalytically active form of a member of zeolites of this invention containing a hydrogenation component, reforming stocks can be reformed employing a temperature between 700° and 1000° F. The pressure can be between 100 and 1000 psig, but is preferably between 200 and 700 psig. The liquid hourly space velocity is generally between 0.1 and 10, preferably between 0.5 and 4 and the hydrogen to hydrocarbon mole ratio is generally between 1 and 20 preferably between 4 and 12.

The catalyst can also be used for hydroisomerization of normal paraffins, when provided with a hydrogenation component, e.g., platinum. Hydroisomerization is carried out at a temperature between 200° and 700° F, preferably 300° to 550° F, with a liquid hourly space velocity between 0.1 and 2, preferably between 0.25 and 0.50 employing hydrogen such that the hydrogen to hydrocarbon mole ratio is between 1:1 and 5:1. Additionally, the catalyst can be used for olefin isomerization employing temperatures between 30° and 500° F.

Other reactions which can be accomplished employing the catalyst of this invention containing a metal, e.g., platinum, including hydrogenation-dehydrogenation reactions and desulfurization reactions. In order to more fully illustrate the nature of the invention and the manner of practicing the same, the following examples are presented.

EXAMPLE 1

This example shows that crystal growth, without nucleation can be effected at low $TPA/SiO_2$ ratios and that zeolites having the ZSM-5 structure can be prepared from reaction mixtures essentially free of aluminum.

To a stirred mixture of 63.3 g of Q-brand sodium silicate in 79.2 g of water at 100° C was added a solution of 12.3 g of tetrapropylammonium (TPA) bromide, 8.7 g of NaBr, and 4.8 g of $H_2SO_4$ in 120 g of water. The reaction mixture had the following molar composition:

$TPA/SiO_2 = 0.15$
$SiO_2/Al_2O_3 = 1400$
$H_2O/OH = 220$
$OH/SiO_2 = 0.20$
$M_2O/SiO_2 = 0.48$

Nucleation of ZSM-5 occurred after 7 days (stirred, 100° C). After 10 days a sample of the solid phase was essentially 100 percent crystalline ZSM-5; it had a crystal size of 0.2–0.6 $\mu$.

To the reaction mixture was then added 100 g of water, followed by a solution of 126.6 g of Q-brand in 158 g of water and finally a solution of 13.4 g of NaBr and 9.6 g of $H_2SO_4$ in 140 g of water. A new gel formed which was stirred for 4 additional days. In this manner the TPA level of the mixture was reduced to give a composition:

$TPA/SiO_2 = 0.05$
$SiO_2/Al_2O_3 = 1400$
$H_2O/OH = 220$
$OH/SiO_2 = 0.27$
$M_2O/SiO_2 = 0.54$

After these 4 days the mixture was filtered and washed free of extraneous salts with water. The solid was ZSM-5 in essentially 100 percent crystallinity. Scanning electron micrographs showed that the crystals had now grown to about 1 $\mu$ in diameter. There was no evidence of new, small crystals ($< 0.2$ $\mu$).

EXAMPLE 2

This example shows that a $TPA/SiO_2$ ratio $> 0$ is necessary for satisfactory growth.

To a stirred mixture of 74.3 g of Q-brand sodium silicate in 80 g of $H_2O$ at 98° C was added a solution of 7.4 g of $H_2SO_4$, 3.8 g of TPABr, and 0.8 sodium tartrate in 159 g of $H_2O$. After thorough mixing, 7.7 g of ZSM-5 crystals were added (1–5 $\mu$, 0.76 percent N, 0.95 percent Na, $SiO_2/Al_2O_3 = 73.9$). The reaction mixture, exclusive of the seed crystal, had a composition as follows:

$SiO_2/Al_2O_3 > 1000$
$H_2O/OH = 450$
$OH/SiO_2 = 0.10$
$M_2O/SiO_2 = 0.29$
$R_2O/M_2O = 0.07$
$TPA/SiO_2 = 0.04$

Stirring was continued for 5 days where upon the mixture was filtered to yield 19 g of ~100 percent crystalline ZSM-5.

When, in a similar experiment, the TPABr was replaced by an equimolar amount of NaBr, the product after 5 days was only about 25 percent crystalline, a crystallinity attributed to the initial seeds.

EXAMPLE 3

This example shows that complexing ligands can effectively remove aluminum from crystallizing gels.

A reaction mixture having the following composition was placed in a steam box to crystallize:

$SiO_2/Al_2O_3 = 90$
$H_2O/OH = 450$
$OH/SiO_2 = .10$
$M_2O/SiO_2 = .48$
$R_2O/M_2O = .16$

Such a mixture would normally yield a ZSM-5 product of $SiO_2/Al_2O_3 \cong 66$ in 17 days.

After 11 days a sample was taken, filtered, and the solid was analyzed by X-ray diffraction. It was 50 percent crystalline ZSM-5. To the remaining mixture was then added a solution of 0.7 g sodium gluconate in 20 cc of water, a molar amount of gluconate equal to all the aluminum originally added. After 12 days the solid phase was 95 percent crystalline ZSM-5 and had a $SiO_2/Al_2O_3$ of 131.

EXAMPLES 4–20

In these examples are summarized results for a range of reaction mixture compositions and crystallization conditions.

Pre-formed, purified cyrstals of ZSM-5 of $SiO_2/Al_2O_3 = 72$ were used in order to separate the processes of nucleation and of growth. The $SiO_2/Al_2O_3$ in these ranged from 67.9 to 79.7. All gels were prepared from Q-brand sodium silicate (28.5% $SiO_2$, 7.75% $Na_2O$). In a typical preparation a solution of 48.3 g of Q-brand and 52.0 g of water was added to a polypropylene bottle immersed in an oil bath at about 100° C. Attached to the bottle was a reflux condenser and a teflon stirring blade and shaft. A solution of 2.5 g of $H_2SO_4$, 1.2 g of TPABr (tetrapropylammonium bromide) and 0.5 g of Na-tartrate in 103 g of water was added with stirring, followed by 5 g of powdered crystalline ZSM-5 aluminosilicate zeolite. The reaction mixture, exclusive of the ZSM-5 zeolite added, had the following mole ratios:

$SiO_2/Al_2O_3 = > 1000$
$H_2O/OH^- = 150$
$OH/SiO_2 = 0.30$
$M_2O/SiO_2 = 0.28$ where M is sodium and tetrapropylammonium cations.

Samples were periodically removed by suction, were filtered, washed, dried and analyzed by X-ray for crystallinity. After 8 days, the mixture was 100% crystalline. It was filtered, boiled with water to remove extraneous salts, was filtered, dried and analyzed.

In these examples (4–20) there are three criteria for successful crystallization, namely, an increased product weight from that of the original seeds, substantial retention of crystallinity, and an increase in $SiO_2/Al_2O_3$ ratio. None of the attempts without added TPA met these criteria, while those with TPA were all successful. The following Table 6 lists the results.

TABLE 6

GROWTH OF ZSM-5 SEED CRYSTALS IN $SiO_2$-ONLY REACTION MEDIA*

| Example | $H_2O/OH$ | $OH/SiO_2$ | $M_2O/SiO_2$ | $R/SiO_2$ | Time Days | Seeds | Product Weight | Product Crystallinity | Product $SiO_2/Al_2O_3$ |
|---|---|---|---|---|---|---|---|---|---|
| 4 | 450 | 0.10 | 0.28 | 0.02 | 10 | 5 g | 13 g | 70% | 193 |

TABLE 6-continued

GROWTH OF ZSM-5 SEED CRYSTALS IN $SiO_2$-ONLY REACTION MEDIA*

| Example | $H_2O/OH$ | $OH/SiO_2$ | $M_2O/SiO_2$ | $R/SiO_2$ | Time Days | Seeds | Product Weight | Crystallinity | $SiO_2/Al_2O_3$ |
|---|---|---|---|---|---|---|---|---|---|
| 5 | 450 | 0.10 | 0.28 | 0 | 10 | 5 | 31 | 30 | 211 |
| 6 | 450 | 0.30 | 0.28 | 0.02 | 5 | 5 | 9 | 100 | 148 |
| 7 | 450 | 0.30 | 0.28 | 0 | 10 | 5 | 12 | 40 | 120 |
| 8 | 150 | 0.30 | 0.28 | 0.02 | 8 | 5 | 9 | 100 | 151 |
| 9 | 150 | 0.30 | 0.28 | 0.02 | 7 | 20 | 22 | 100 | 102 |
| 10 | 150 | 0.30 | 0.28 | 0 | 14 | 5 | — | — | — |
| 11 | 100 | 0.60 | 0.32 | 0.02 | 13 | 5 | 7 | 100 | 90 |
| 12 | 100 | 0.60 | 0.31 | 0 | 13 | 5 | 5 | 100 | 69 |
| 13 | 150 | 0.30 | 0.28 | 0.02 | 3 | 10 | 22 | 70 | 153 |
| 14 | 150 | 0.30 | 0.28 | 0 | 3 | 10 | 20 | 50 | 134 |
| 15 | 450 | 0.10 | 0.28 | 0.02 | 4 | 10 | 34 | 100 | 217 |
| 16 | 450 | 0.10 | 0.27 | 0 | 15 | 10 | 35 | 25 | 202 |
| 17 | 150 | 0.30 | 0.28 | 0.02 | 7 | 20 | 21 | 100 | 98 |
| 18 | 150 | 0.30 | 0.28 | 0 | 18 | 20 | — | 70 | 89 |
| 19 | 150 | 0.30 | 0.28 | 0.02 | 6 | 20 | 25 | 100 | 94 |
| 20 | 150 | 0.30 | 0.28 | 0 | 14 | 20 | — | 70 | 74 |

*All stirred at 200–300 rpm
Examples 4 to 12 were as synthesized, large crystal seeds, 100° C
Examples 13 and 14 were as synthesized, large crystal seeds, 160° C
Examples 15 to 18 were calcined, $NH_4$-form, large crystals, 100° C
Examples 19 and 20 were as synthesized, microcrystalline seeds, 100° C

EXAMPLES 21 and 22

These examples illustrate procedures for synthesizing layered ZSM-5 crystallites without separation and purification of the aluminum-containing intermediate product. The experiments are detailed in Table 7.

Both examples were preceded by nucleation for 7 days in a reaction mixture as specified in the Table. This reaction mixture produced a ZSM-5 product having a $SiO_2/Al_2O_3$ ratio = 72 and thereby removed, in addition to aluminum, 0.238 moles of $SiO_2$ together with about 0.005 moles of TPA and of Na cations. At this point, additional reactants were added but with no further TPA. In this manner, the effective $TPA/SiO_2$ ratio of the reaction mixture was reduced from 0.15 to 0.05. Following an additional 7 days of crystallization, the experiment designated Examples 21 and 22 were conducted to illustrate the calculations and the procedures. In each case, reaction mixture compositions were calculated after subtracting that material already crystallized.

That the product crystals possess an intact and accessible pore system, if somewhat modified, was demonstrated by measuring sorptive capacities on calcined as-synthesized products. Sorptive capacities for n-hexane, 20 mm, 25° C, were 11.3%, 10.9% and 11.1% for Examples 9, 19 and 21, respectively, vs. 11.1% for untreated ZSM-5's.

EXAMPLE 24

This example shows that ZSM-5 samples treated in accordance with these procedures are useful and are selective in the conversion of hydrocarbons.

The product of Example 9 was calcined in flowing nitrogen to 550° C, cooled, and exchanged with 2M $NH_4NO_3$ to yield the $NH_4$-form of the zeolite. After calcination to 550° C in air, the active zeolite catalyst (sized to 60/80 mesh) was contacted with a five component hydrocarbon feed as follows:

Feed = Equal weight mixture of n-hexane, 3-methylpentane, 2,3-dimethylbutane, benzene and toluene
WHSV = 3.1

TABLE 7

MULTI-STEP CRYSTALLIZATION OF LAYERED ZSM-5 STIRRED, 100° C

| Operation | Moles in Reaction Mixture $SiO_2$ | $Al_2O_3$ | $TPA_2O$ | $Na_2O$ | OH | $H_2O$ | Ratios Exclusive of Zeolite $SiO_2/Al_2O_3$ | $H_2O/OH$ | $OH/SiO_2$ | $M_2O/SiO_2$ | $TPA/SiO_2$ |
|---|---|---|---|---|---|---|---|---|---|---|---|
| Nucleation 7 days | 0.301 | 0.0033 | 0.023 | 0.079 | 0.030 | 13.5 | 90 | 450 | 0.10 | 0.34 | 0.15 |
| Less solid | −0.238 | −0.0033 | −0.005 | −0.005 | −0.007 | — | | | | | |
| Add gel | 0.601 | 0.0066 | 0 | 0.158 | 0.036 | 16.4 | | | | | |
| Growth 7 days | 0.664 | 0.0066 | 0.018 | 0.232 | 0.059 | 29.9 | 101 | 500 | 0.09 | 0.38 | 0.05 |
| Example 21 | | | | | | | | | | | |
| Less solid | −0.475 | −0.0066 | −0.009 | −0.009 | −0.013 | — | | | | | |
| Add gel | 0.301 | 0 | 0 | 0.079 | 0 | 2.3 | | | | | |
| Shell 3 days | 0.490 | 0 | 0.009 | 0.302 | 0.046 | 32.2 | >1000 | 700 | 0.09 | 0.63 | 0.035 |
| Product | [1.04 | 0.011 | 0.021 | 0.057][a] | | | (95) | — | — | — | — |
| Example 22 | | | | | | | | | | | |
| Less solid | −0.475 | −0.0066 | −0.009 | −0.009 | −0.013 | — | | | | | |
| Add gel | 0.601 | 0 | 0 | 0.158 | 0.191 | 4.6 | | | | | |
| Shell 7 days | 0.790 | 0 | 0.009 | 0.381 | 0.237 | 34.5 | >1000 | 150 | 0.30 | 0.49 | 0.02 |
| Product ZSM-5 | [0.97 | 0.010 | 0.018 | 0.022][a] | | | (96) | — | — | — | — |

[a]Material balance obtained on product zeolite

EXAMPLE 23

In Example 23, sorptive properties of layered ZSM-5 products were tested as a measure of channel and crystal integrity.

Temperature = 316° C
$H_2$/Hydrocarbon = 3.6
Pressure = 200 psig

Conversion was measured at 5 and at 25 hours on stream and averaged: hexane = 78%, 3-methylpentane = 15%, 2,3-dimethylbutane = 1%, benzene = 7% and toluene = 4%. During this test reaction, alkylation and rearrangement of aromatics occurs. In this example, over 10% of the paraffins cracked were incorporated into the liquid product as alkyl groups on the feed benzene and toluene. Xylenes, produced in the rearrangement of alkyl aromatics, were found to be unusually high in para-isomers. The molar ratio of para/meta-xylene was 1.1 as compared with a ratio of 0.6 over untreated large crystal ZSM-5 catalysts and a thermodynamically expected ratio of 0.45.

I claim:

1. A composition comprising a crystalline aluminosilicate zeolite having an aluminum-free outer shell of $SiO_2$, said zeolite being made by a two stage method comprising:

(1) initiating crystallization in a crystallization medium to produce the zeolite and (2) altering the crystallization medium to substantially eliminate the aluminum therein said outer shell of $SiO_2$ having the same crystal structure as said zeolite.

2. The composition of claim 1 wherein in step (2) the organic ion to $SiO_2$ ratio is reduced.

3. The composition of claim 1 wherein in step (2) the hydroxide is increased.

4. The composition of claim 1 wherein the zeolite has a constraint index of from 1 to 12.

5. The composition of claim 1 wherein the zeolite is selected from the group consisting of ZSM-5, ZSM-11, ZSM-12, ZSM-21 and ZSM-35.

6. The composition of claim 1 wherein the reaction mixture, to produce the $SiO_2$ outer shell, exclusive of added solid crystals, has the following composition, in terms of mole ratios of oxides:

$R/SiO_2 = 0.01 - 0.10$
$SiO_2/Al_2O_3 = 300 - 5000$
$H_2O/OH^- = 20 - 500$
$OH^-/SiO_2 = 0.05 - 1.0$
$M_2O/SiO_2 = 0.1 - 2$ wherein R is an organic ion and M is a mixture of alkali metal and organic cations.

7. The composition of claim 6 wherein the temperature to form the outer shell is from about 80° C to about 200° C.

8. The composition of claim 7 wherein the time of reaction is from about 4 hours to about 3 days.

9. The composition of claim 6 wherein ZSM-5 is coated with $SiO_2$ and wherein the reaction mixture to yield the coat of $SiO_2$, exclusive of added ZSM-5, has the oxide ratios as follows:

$R/SiO_2 = 0.02$
$SiO_2/Al_2O_3 = >1000$
$H_2O/OH^- = 150$
$OH^-/SiO_2 = 0.30$
$M_2O/SiO_2 = 0.28$ wherein M is a mixture of alkali metal and tetrapropylammonium cations and R is tetrapropylammonium.

10. A method for making a composition comprising a crystalline aluminosilicate zeolite having an aluminum-free outer shell of $SiO_2$ having the same crystal structure as said zeolite, said method comprising the steps of:

(1) initiating crystallization in a crystallization medium to produce the zeolite and (2) altering the crystallization medium to substantially eliminate the aluminum therein.

11. The method of claim 10 wherein the zeolite has a constraint index of 1 to 12.

12. The method of claim 10 wherein in step (2) the organic ion to $SiO_2$ ratio is reduced.

13. The method of claim 10 wherein in step (2) the hydroxide is increased.

14. The method of claim 10 wherein the zeolite is selected from the group consisting of ZSM-5, ZSM-11, ZSM-12, ZSM-21 and ZSM-35.

15. The method of claim 10 wherein the reaction mixture to produce the $SiO_2$ outer shell, exclusive of solid crystals, has the following composition, in terms of moles of ratio of oxides:

$R/SiO_2 = 0.01 - 0.10$
$SiO_2/Al_2O_3 = 300 - 5000$
$H_2O/OH^- = 20 - 500$
$OH^-/SiO_2 = 0.05 - 1.0$
$M_2O/SiO_2 = 0.1 - 2$ wherein R is an organic ion and M is a mixture of alkali metal and organic cations.

16. The method of claim 15 wherein the temperature to form said outer shell is from about 80° C to about 200° C.

17. The method of claim 16 wherein the time of the reaction is from about 4 hours to about 30 days.

18. The method of claim 15 wherein ZSM-5 is coated with $SiO_2$ and wherein the reaction mixture to yield the coat of $SiO_2$, exclusive of added ZSM-5, has oxide ratios as follows:

$R/SiO_2 = 0.02$
$SiO_2/Al_2O_3 = >1000$
$H_2O/OH^- = 150$
$OH^-/SiO_2 = 0.30$
$M_2O/SiO_2 = 0.28$ wherein M is a mixture of alkali metal and tetrapropylammonium cations and R is tetrapropylammonium.

19. The method of claim 10 wherein any remaining aluminum ion in the reaction mixture to form the zeolite is complexed and removed.

20. The method of claim 19 wherein the complexing agent is selected from the group consisting of gluconic acid, tartic acid, nitrilotriacetic acid and ethylenediaminetetraacetic acid.

* * * * *

UNITED STATES PATENT AND TRADEMARK OFFICE
CERTIFICATE OF CORRECTION

PATENT NO. : 4,088,605

DATED : May 9, 1978

INVENTOR(S) : LOUIS D. ROLLMANN

It is certified that error appears in the above-identified patent and that said Letters Patent are hereby corrected as shown below:

| | |
|---|---|
| Column 7, Table col. 1 (second ratio) | Numbers should be lined up. |
| Column 7, line 28 | "90°" should read --90°C--. |
| Column 8, Second Table col. 1 (second ratio) | Numbers should be lined up. |
| Column 8, line 64 | "90°" should read --90°C--. |
| Column 8, line 66 | "150°" should read --150°C--. |
| Column 10, line 58 | "80°" should read --80°C--. |
| Column 10, line 65 | "80°" should read --80°C--. |
| Column 11, line 19 | "150°" should read --150°F--. |
| Column 11, line 21 | "500°" should read --500°F--. |
| Column 12, line 34 | "400°" should read --400°F--. |
| Column 12, line 41 | "550°" should read --550°F--. |
| Column 12, line 47 | "700°" should read --700°F--. |
| Column 12, line 63 | "30°" should read --30°F--. |
| Columns 15 and 16, Table 7 (col. 1 under Example 21) | "Product" should read --Product ZSM-5--. |
| Column 16, line 35 | "2M" should read --2<u>M</u>--. |
| Column 17, Claim 8 | "3 days" should read --30 days--. |

Signed and Sealed this

*Nineteenth* Day of *December 1978*

[SEAL]

*Attest:*

RUTH C. MASON
*Attesting Officer*

DONALD W. BANNER
*Commissioner of Patents and Trademarks*